US010463047B2

(12) United States Patent
Mäki et al.

(10) Patent No.: US 10,463,047 B2
(45) Date of Patent: Nov. 5, 2019

(54) ANTIMICROBIAL IONOMER COMPOSITION AND USES THEREOF

(71) Applicant: ARGENLAB GLOBAL LTD, Valletta (MT)

(72) Inventors: Markus Mäki, Helsinki (FI); Jyri Nieminen, Helsinki (FI); Harri Laaksonen, Tampere (FI); Sami Areva, Tampere (FI)

(73) Assignee: Argenlab Global Ltd, Valletta (MT)

( * ) Notice: Subject to any disclaimer, the term of this patent is extended or adjusted under 35 U.S.C. 154(b) by 0 days.

(21) Appl. No.: 15/366,130

(22) Filed: Dec. 1, 2016

(65) Prior Publication Data

US 2017/0079275 A1    Mar. 23, 2017

Related U.S. Application Data

(63) Continuation of application No. 14/240,033, filed as application No. PCT/FI2012/050803 on Aug. 22, 2012, now abandoned.

(60) Provisional application No. 61/525,888, filed on Aug. 22, 2011.

(30) Foreign Application Priority Data

Aug. 22, 2011   (FI) ...................... 20115816

(51) Int. Cl.
| | |
|---|---|
| *A01N 55/02* | (2006.01) |
| *A01N 59/16* | (2006.01) |
| *C08K 3/16* | (2006.01) |
| *A01N 25/22* | (2006.01) |
| *A01N 25/08* | (2006.01) |
| *A41D 13/12* | (2006.01) |
| *C09D 133/08* | (2006.01) |
| *C09D 5/14* | (2006.01) |
| *C10M 161/00* | (2006.01) |

(52) U.S. Cl.
CPC ............. *A01N 55/02* (2013.01); *A01N 25/08* (2013.01); *A01N 25/22* (2013.01); *A01N 59/16* (2013.01); *A41D 13/1209* (2013.01); *C08K 3/16* (2013.01); *C09D 5/14* (2013.01); *C09D 133/08* (2013.01); *C10M 161/00* (2013.01); *A41D 2500/10* (2013.01); *C10M 2201/06* (2013.01); *C10M 2217/02* (2013.01); *C10N 2230/16* (2013.01)

(58) Field of Classification Search
CPC ........ A01N 55/02; A01N 59/16; A01N 25/22; A01N 25/08; C08K 3/16; A41D 13/1209; A41C 2500/10; C09D 5/14; C09D 133/08; C10M 161/00; C10M 2201/06; C10M 2217/02; C10N 2230/16
See application file for complete search history.

(56) References Cited

U.S. PATENT DOCUMENTS

| | | | |
|---|---|---|---|
| 6,224,898 | B1 | 5/2001 | Balogh et al. |
| 8,524,796 | B2 | 9/2013 | Kim |
| 2005/0112151 | A1 | 5/2005 | Horng |
| 2005/0117112 | A1 | 6/2005 | Nayiby |
| 2005/0152955 | A1 | 7/2005 | Akhave |
| 2009/0149583 | A1 | 6/2009 | Lin et al. |
| 2009/0246258 | A1 | 10/2009 | Shukla et al. |

FOREIGN PATENT DOCUMENTS

| | | |
|---|---|---|
| JP | 2001508041 A | 6/2001 |
| JP | 2007535573 A | 12/2007 |
| JP | 2010184883 A | 8/2010 |
| JP | 2012224563 A | 11/2012 |
| WO | WO 98/18330 A1 * | 5/1998 |
| WO | WO9818330 A1 | 5/1998 |
| WO | WO0015036 A1 | 3/2000 |
| WO | WO 2002/30204 A1 * | 4/2002 |
| WO | WO0230204 A1 | 4/2002 |
| WO | WO2005107455 A2 | 11/2005 |
| WO | WO2010083589 A1 | 7/2010 |
| WO | WO2010108837 A1 | 9/2010 |

* cited by examiner

*Primary Examiner* — Blessing M Fubara
(74) *Attorney, Agent, or Firm* — Seppo Laine Oy; Mark W. Scott

(57) ABSTRACT

The invention concerns a polymeric antimicrobial composition, a method of producing the same and the uses thereof. The ionomer composition comprises an amine functional polymer compound reacted with silver halide, optionally together with a stabilizing component, such as an organic substance carrying a sulfonamide functional group. The ionomer composition can be obtained by reacting together (i) at least one polyamine and silver halide and optionally at least one organic stabilizer substance or; (ii) at least one polyamine, at least one non-halide silver salt or silver complex, hydrogen halide and/or alkaline metal halide salt and optionally at least one organic stabilizer substance. The present ionomer composition is suitable for use as an antimicrobial coating, antimicrobial finish, antimicrobial additive and as antimicrobial component for formation of new antimicrobial materials.

15 Claims, No Drawings

ANTIMICROBIAL IONOMER COMPOSITION AND USES THEREOF

BACKGROUND OF THE INVENTION

Field of the Invention

The present invention relates to polymeric antimicrobial compositions. In particular the invention concerns novel antimicrobial ionomer compositions, methods of preparing the same and the uses thereof.

Description of Related Art

Antimicrobial technologies based on the bioactive properties of ionic silver are currently widely recognized as belonging to the most advanced solutions on the wide application field of antimicrobial materials both in the science community and the industries utilizing antimicrobial surface technologies. Ionic silver has a general status as a safe biocide in many applications. Also the wide antimicrobial spectrum of silver against most bacterial species, including the antibiotic resistant strains, e.g. MRSA and NDM-1 which currently generate a severe health treat to patients in the form of hospital infections, makes ionic silver particularly interesting.

Recently in the healthcare sector, strategies for improving hospital hygiene and preventing infections have been extended to cover the aspect of spreading of infections through various surfaces in the healthcare environments. Correspondingly the application of antimicrobial materials and coating technologies have been emphasized as a new complementary mean for together with other aspects contributing to the battle against hospital infections.

Multiple strategies have been utilized to form antimicrobially active, silver releasing surfaces on fibers and bulk material surfaces. Conventional strategies typically comprise attachment on the surfaces of silver containing particles, such as nanosilver, silver zeolite, silver zirconium phosphate and silver chloride containing titanium dioxide particles, by various chemical means, typically utilizing a carrier material. Another conventional method is to treat certain surface materials chemically in order to provide attachment of silver ions or silver containing particles on the surface.

Nanoparticulate silver (nanosilver) has recently been extensively studied emerged as a potentially hazardous material to health and environment, which again has increased pressure towards developing of new silver ion technologies Liquid antimicrobial additives for liquid products, such as disinfection solutions, surfactants, paints, wax/polymer coatings, deodorizing solutions and cosmetic solutions, are typically based on utilization of silver citrate solutions or silver zeolite or particulate silver dispersions, colloidal silver.

To date, polymer carrier based silver technologies have not been studied or developed extensively. Technologies based on functional ionic polymers are rare.

International Published Patent Application WO2002/030204 discloses novel antibacterial agents, wherein the lone pair electrons of nitrogen atoms of amine compounds with high boiling point or water-soluble polymer with basic nitrogen at the backbone or side chain are coordinated with silver ion. Antibacterial and deodorizing solution comprising them are also disclosed.

US Published Patent Application No. 2009246258 discloses antimicrobial and odor adsorbing fabric substrate having a surface coating. The coating contains silver compounds and combination thereof, a hyperbranched polyethyleneimine derivative, potassium citrate, inorganic chloride, a polyurethane binder, and a cross-linking agent. The silver compounds are selected from the group consisting of silver zirconium phosphate, silver zeolite, silver glass, and any mixtures thereof or a conductive silver containing nanoparticles. ion-exchange resins, zeolites, or, possibly substituted glass compounds.

According to the publication hyperbranched polyethyleneimine derivative, abbreviated "h-PEI", comprises at least one hyperbranched polyethyleneimine linked to one or more linear hydrocarbon groups having 5 to 30 carbons. The preferred silver containing compounds are silver zirconium phosphate available from Milliken & Company under the trade name ALPHASAN, silver zeolite available from Sinanen under the trade name ZEOMIC, and silver glass available from Ishizuka Glass under the trade name ION-PURE. Inorganic chlorides are preferred, especially magnesium chloride and ammonium chloride. A range of ratios from 1:10 to 5:1 (chloride to silver ion). The h-PEI derivatives also suffered from discoloration and it was found that potassium citrate reduced or eliminated the yellowing of the h-PEI.

SUMMARY OF THE INVENTION

The present invention aims at providing an antimicrobial ionomer composition, which comprises an amine functional cationic polymer and silver halide.

According to the invention, an antimicrobial amorphous ionomer composition can be obtained by a process comprising reacting at least one amine functional polymer and a silver halide. Alternately, the composition can be obtained by a process comprising reacting a amine functional polymer and at least one silver non-halide salt or complex compound and hydrogen halide or an alkali metal or alkaline earth metal or ammonium halide salt.

Thus, in a first preferred embodiment the antimicrobial ionomer composition is obtained by reacting together in a solvent matrix
  at least one polymer exhibiting functional amine groups, and
  a silver halide.

In another preferred embodiment, the present antimicrobial ionomer composition is obtained by reacting together in a solvent matrix
  at least one polymer exhibiting functional amine groups,
  at least one organic silver salt or complex compound and
  hydrogen halide, an alkali metal or alkaline earth metal halide salt or ammonium halide salt, or a combination thereof.

In further preferred embodiments, the present antimicrobial ionomer composition is further balanced and controlled by including stabilizing components in the composition. In further preferred embodiments, the stabilizing components comprise a sulfonamide group containing organic substance (s). In some embodiments, said stabilizer substance may be the counter-anion or ligand of said at least one organic silver salt or complex compound.

In some embodiments, said antimicrobial composition includes additional components, such as cross-linking agents, hydrophobic modifiers, water repellents, various stabilizers and surfactants.

The preparation methods disclosed above can also be combined.

The antimicrobial ionomer composition according to the invention can be used for coating and treating a great variety of host surfaces.

More specifically, the present ionomer compositions are mainly characterized by what is stated in the characterizing part of claim 1.

The method according to the present invention is characterized by what is stated in the characterizing part of claim 25.

The use of the ionomer compositions is characterized by what is stated in claim 31.

The invention provides considerable advantages. Generally, the novel composition is suitable for use as an antimicrobial coating, antimicrobial and sanitizing finish, antimicrobial additive and as antimicrobial component for formation of new antimicrobial materials.

The novel antimicrobial ionomer compositions are particularly useful for coating of various substrates, such as fiber, fabric and bulk material surfaces, including various synthetic, semisynthetic and natural fibers, woven fabrics, nonwoven fabrics, knitted fabrics, papers, various polymer surfaces, metal surfaces, various coating surfaces, wood surfaces and fibers. The novel antimicrobial ionomer compositions are particularly useful for antimicrobial wet wipes, hand sanitizer liquids and cosmetics.

The ionomer composition according to the present invention provides an enhanced antimicrobial effect, optical performance and stability which surpasses that of known antibacterial compositions comprising different silver sources mixed with polyamine polymers. It appears that halide carrying ionomers of polyamine and silver provide enhanced adhesion properties, antimicrobial activity, control of silver-ion release and optical performance. The ionomer composition according to the present invention is preferably free of particles.

Next the invention will be examined more closely with the aid of a detailed description and with reference to a number of working examples.

DETAILED DESCRIPTION OF PREFERRED EMBODIMENTS

The present invention discloses novel antimicrobial compositions comprising ionomers of amine functional polymers (i.e. polymers exhibiting functional amine groups) and metal halides. According to a preferred embodiment of the ionomer composition according to the invention, the composition is produced in—and it therefore also comprises—a solvent matrix, preferably comprising alcohols, such as methyl alcohol or ethyl alcohol, isopropyl alcohol or water and combinations thereof.

In a first preferred embodiment, the ionomer compositions are obtained by reacting together at least one amine functional polymer (ionomer prepolymer, carrier polymer) and silver halide. In another preferred embodiment the ionomer compositions are obtained by reacting together at least one amine functional polymer (ionomer prepolymer, carrier polymer), at least one non-halide silver salt or complex compound and hydrogen halide and/or alkali metal or alkaline earth metal (in the following jointly designated "alkaline metal") halide salt.

In one embodiment, an amine functional polymer "carrier" polymer is reacted together with either silver halide or a silver salt or complex compound, however in the latter case the composition is halidized with either hydrogen halide or alkaline metal halide salt ("halide compound") in order to obtain the composition characteristic to the invention. In a preferred embodiment, at least one stabilizer component/substance is included in the system (composition). With both routes the obtained product possesses similar essential properties independent of variations in the proton or alkaline metal cation or alkaline metal salt concentrations.

In a preferred embodiment of the invention, said amine functional ionomer prepolymer comprises a branched polyethyleneimine, a linear polyethyleneimine or a mixture of corresponding polyethyleneimines of different qualities with different properties with regard to e.g. molecular weights and primary:secondary:tertiary-amine ratios. Also copolymers of polyethyleneimines are useful.

In other embodiments said amine functional polymer comprises other linear or branched polyamines, such as polyvinylamine, polyacrylamine, polyarylamine, polyethyleneimine, polyhexamethylene-biguanidine and polyvinylpyridine. Combinations of various amine functional polymers may be applied for obtaining the antimicrobial ionomer compositions characteristic to the invention.

The amine functional polymer preferably comprises or consists of or consists essentially of a potentially branched polyethyleneimine having a molecular weight (Mw) between 200 and 3,000,000, in particular about 750 to 2,000,000.

As further examples, the following embodiments can be mentioned:

compositions wherein the amine functional polymer is polyvinylamine or copolymer having 30-100 mol-% of vinylamine, in particular embodiments wherein the amine functional polymer is graft polymer of polyvinylamine with ethyleneimine;

compositions wherein the amine functional polymer is a graft polymer of polyamidoamine with ethyleneimine;

compositions wherein the amine functional polymer is a polyarylamine copolymer; and compositions wherein the amine functional polymer is polyacrylamine.

Compositions wherein the polymer components are internally cross-linked through at least one cross-linking agent are also contemplated.

In some embodiments, said stabilizer component comprises one or more organic or inorganic substances capable of promoting the stability of silver moieties within the composition against various stressors, such as UV radiation, heat, moisture, redox reactions, pH and other factors which may cause unfavorable changes to the compositions in accordance with the invention. The unfavorable effects include discoloration, particle formation and other unfavorable effects in the essential chemical structure of the compositions and correspondingly e.g. in the state appearance of the composition.

In one preferred embodiment of the invention, said stabilizer comprises at least one substance or compound carrying sulfonamide functional group(s).

In another preferred embodiment, said stabilizer comprises ammonium cations.

In another preferred embodiment, said stabilizer comprises excess chloride anions.

In another preferred embodiment, said stabilizer substance or combination of stabilizer substances is selected from the group comprising saccharin, cyclamic acid, sulfadiazine, acesulfame, ammonium chloride and ammonium saccharin.

In a particularly preferred embodiment said stabilizer substance comprises saccharin.

In some embodiments said stabilizer substance may comprise e.g. organic acids (such as carboxylic acids, sulfonic acids and amino acids), quarternary ammonium compounds, phosphates, esters, aldehydes, ketones, zwitterionic compounds, titanates and their organic derivatives, silanes and their organic derivatives and organosulphur compounds.

Saccharin (o-sulfobenzimide; 1,2-benzothiazole-3(2H)-one 1,1-dioxide) is one of the most widely used artificial sweetening agents. The imino hydrogen of saccharin is acidic. The molecule can easily be converted into the corresponding nitranion. The coordination chemistry of the saccharinato anion is very versatile. It offers multiple coordination sites to metallic centers.

A typical silver compound, silver saccharinate (usual form: silver saccharinate dihydrate) is a solid white powder with limited solubility properties. Silver saccharin may typically be produced through precipitation by reacting acidic form saccharin and silver nitrate, or from sodium saccharin and silver nitrate in certain solvent compositions depending on the molecular state of saccharin.

In some embodiments, the free amine functional groups of said amine functional polymer, which in a preferred embodiment comprises polyethyleneimine, have a function in attachment of said composition to host materials (materials wherein the ionomer composition of the invention is added to provide antimicrobial functionality) and material surfaces (surfaces coated with material comprising the ionomer composition of the invention). When used as an additive, attachment to host material/host matrix may be achieved through adhesion, e.g. ionic bonding or covalent bonding, between amine groups of the amine functional polymer backbone part of the ionomer composition according to the invention and a molecular structure of a second material or interactions the like.

In one preferred embodiment the solvent matrix comprises ethyl alcohol or methyl alcohol or isopropanol or water or combinations thereof. Mixtures of solvents may be used, such as aqueous alcoholic solutions/mixtures. Said antimicrobial ionomer composition can be extracted from said solvent matrix for further use e.g. through evaporating the solvent. Typically a more practical and economical solution is, however, to design further processes for using the composition directly with a solvent matrix containing the ionomer composition as a starting material.

According to another embodiment of the invention, the silver cation is delivered into the onomer composition as a non-halide silver salt or silver complex, which reacts with amine functional polymer(s), in a preferred embodiment polyethyleneimine, followed by chloridization of the composition with hydrogen halide or alkaline metal halide salt or combinations thereof. In association with the latter embodiment, suitable non-halide silver salts or silver complexes include e.g. silver nitrate, silver acetate, silver stearate, silver oxide, silver saccharinate, silver imidazole, silver citrate, silver methacrylate and silver sulfadiazine. In some embodiments, the chemical properties of the counter-ions (anions) of the specific silver salts are utilized in stabilization of the composition and in controlling the migration of silver ions from the composition.

The silver content of the ionomer composition is about 0.001 to 50%, in particular about 0.01 to 30%, preferably about from 1 or 1.5 up to 25% by weight of the total dry weight of the composition. The dry weight in this case is defined as the total weight of the composition when the mass of the solvent matrix is excluded from the calculation.

In a preferred embodiment, the ionomer composition according to the invention is obtained by a process, which comprises the following steps:

First, an alcoholic or aqueous solution of polyethyleneimine (PEI) is provided. In some embodiments, the optimal ratio (w/w) between PEI and solvent ranges from 1:0.01 to 1:100, in particular from 1:0.5 to 1:5, depending on the desired amount of the ionic silver compound, which is to be fed into the solution in the next step. Also, the assessment of the optimal solvent ratio depends on the molecular weight of polyethyleneimine to be used and the viscosity of the solution. The reaction between PEI and solvent is typically exothermic. In a preferred embodiment, the mixture is cooled to standard temperature or below (i.e. the mixture is cooled to 25° C. or less, typically however to a temperature above the melting point of the liquid part of the mixture).

Next a solid ionic silver source is fed into the solution and mixed. E.g. silver halide reacts with PEI solution while increase of viscosity indicates ionomer formation. Depending on silver content and PEI:solvent ratio, a transparent, yellowish or almost colorless silver ionomer composition is formed.

The silver content of the ionomer composition may be controlled by regulating the amount of the silver source reacted with the PEI-solution, in one embodiment silver chloride. Typically the silver compound is used at 0.1 to 10,000 parts by weight, preferably about 1 to 1,000 parts by weight, for example 10 to 100 parts by weight for each 100 parts by weight of the ionomer prepolymer. Thus, typically the weight ratio of the silver compound to the ionomer prepolymer is about 1:100 to 100:1, in particular 1-10:50-100.

Particularly preferred embodiments comprise reacting together 70 to 99.99 parts by weight of ionomer prepolymer and 0.01 to 30 parts by weight of a silver halide or of a complex compound and hydrogen halide, or of alkaline metal or ammonium halide salt.

Optionally thereafter a stabilizer compound, in a preferred embodiment acid form saccharin and/or sodium saccharin and/or potassium acesulfame, is fed into the composition. When mixed together with the ionomer solution formed by the PEI and silver chloride, said acid form saccharin or sodium saccharin solubilizes into the ionomer solution forming a stable ionomer composition. The stabilizer compound is used in amounts of 1 to 50 parts by weight for each 100 parts by weight of the combination of the silver compound with the polymer compound. Typically, the weight ratio between the silver compound and the stabilizer compound is about 1:10 to 10:1.

A preferred embodiment comprises reacting together 50 to 98.99 parts by weight of ionomer prepolymer, 0.01 to 30 parts by weight of a silver compound, or combination of silver compound and a halide compound, as explained above, and 1 to 20 parts by weight of a stabilizer.

In another preferred embodiment, a solution of PEI and alcoholic or aqueous solution is first produced and cooled down as described previously. Thereafter solid silver saccharin is delivered into the polymer solution and mixed. Silver saccharin solubilizes into the PEI solution and forms a transparent, yellowish or almost colorless solution of silver ionomer complex. The silver content of the composition may be controlled e.g. through the amount of silver saccharin.

Thereafter, in a preferred embodiment, an aqueous solution of hydrochloric acid is supplied. In one preferred embodiment the molar amount of the chloride anion is equivalent to the molar amount of silver cations. When the solution of PEI and silver saccharin is chloridized, a momentary white precipitation can be observed suggesting that at least a part of the silver cation is precipitated from the soluble PEI-silver complex by the chloride anion, however, the assumed silver chloride precipitation is quickly reacted further. The latter phenomenon also suggests that silver chloride has a tendency to form unique ionic bonds with the amine functional groups of polymers. However, this is only one possible explanation for the observed phenomenon and should not interpreted as in any way limiting on the scope of the invention.

The molecular structure of the silver cation source, typically a silver salt or complex, has naturally a role in production of silver ionomer, through the introduction of the corresponding counter-ion (anion) or ligand into the system and through the specific interactions with the ionomer composition.

An interesting phenomenon observed in association with the invention at hand is, that surprisingly, the presence of halide anions, in a preferred embodiment, chloride anions, in the amine functional silver ionomer produces an enhanced antimicrobial effect when compared to ionomers comprising solely a PEI having its amine groups reacted with silver ions.

In a preferred embodiment, polyethyleneimines (PEIs) are applied as amine functional polymers in accordance with the invention. PEIs belong to the class of polyamines and cationic polymers having the highest cationic charges per weight. The structures of homopolymeric polyethyleneimines always follow the pattern: one amine nitrogen and two carbon groups.

In general, PEIs adhere to various polar surfaces very effectively. Branched PEIs comprising cationic anchor points (amines) allow fixation of the molecules to various surfaces and substrates with exceptionally high adhesion. In some embodiments of the invention, the amine groups of the ionomer composition may be cross-linked to various surfaces. Resulting from the strong surface active character, the ionomer composition according to the invention can be applied as e.g. an additive in substrates and adhesives and as building blocks in a polymer matrix. Like amine functional polymers, the ionomer compositions according to the invention are soluble in polar solvents and miscible with e.g. water, ethyl alcohol and methyl alcohol at any concentration.

In some embodiments the properties of the ionomer composition according to the invention are controlled through chemically bonding the amine groups of the amine functional polymer according to the composition with various additive compounds and compositions suitable for a specific application of the ionomer composition. In some embodiments, the additives may include anionic, non-ionic and other non-covalently bonded compounds (such as non-ionic surfactants, conjugate bases of carboxylic acids, zwitterionic compounds etc.) or organic compounds (e.g. epoxy or isocyanate functionalized organic compounds) covalently bonded with the amine groups of the composition.

In some embodiments, the ionomer compositions according to the invention may be cross-linked internally and/or to and/or within host surfaces, materials and compositions. In some embodiments, the applicable cross-linking agents include e.g. substances with isocyanate, epoxy, aziridine, titanate, silane and acrylate functionalities.

The present antimicrobial ionomer compositions, when supplied in a liquid matrix, have a dry matter concentration of 0.0001 to 99% by weight, in particular about 0.001 to 90% by weight, advantageously 0.01 to 75% be weight, calculated from the total weight of the composition. As the below working examples show, the composeitions can readily be manufactured to a dry matter content of about 0.1 to 50% by weight of the total weight of the composition. Such compositions can be concentrated or, usually diluted with further liquid, for the intended applications.

Based on the above, in a first embodiment a composition according to the present invention comprises, or alternatively consists of, 70 to 99.99% (by weight) of polymer and 0.01 to 30% (by weight) of a silver compound, such as a silver salt, in particular silver halide, for example AgCl. The percentages are calculated from the total weight of the dry matter of the composition. Typically, said composition is free from stabilizing compounds.

In a second embodiment, a composition according to the present invention comprises, or alternatively consists of, 50 to 98.99% (by weight) of polymer, 0.01 to 30% (by weight) of a silver compound, such as a silver salt, in particular silver halogenide, for example AgCl, and 1 to 20% (by weight) of a stabilizer. The percentages are calculated from the total weight of the dry matter of the composition (i.e. w/w).

The latter composition is particularly suitable as a concentrate which can be diluted into a liquid, such as an alcohol, typically an aliphatic alcohol having 1 to 6 carbon atoms.

When a composition, for example a concentrate produced in alcohol, is diluted in water, further stabilizer may be added. Generally, the total concentration of stabilizers in aqueous phase can be up to 95% w/w. An example of a particularly suitable additional stabilizer is ammonium chloride.

Through the adhesive character of the ionomer composition according to the invention at hand, the composition functions well as thin films and monomolecular layers. Retrieved from the properties of PEIs, 1 mg of the ionomer composition according to the invention may cover an area of close to 2 $m^2$ of a nonporous surface with a monomolecular layer.

Generally, the applied amount of the present ionomer composition will be dependent on the aimed concentration of silver on the host surface. Typically, a silver concentration of about 0.001 to 10% of the total weight of the coating layer on the substrate is sufficient.

The ionomer compositions according to the invention are directly compatible with cationic or nonionic systems. The PEI-backbone with cationic amine groups may break down anionic dispersions or naturally depending on the chemical environment, produce modified dispersions or emulsions containing the composition according to the invention. Anionic surfaces adhere strongly to the composition due to ionic charges. In some embodiments, anionic or nonionic additives may be incorporated into the composition according to the invention for enhancing and improving compatibility of the ionomer composition with e.g. anionic systems.

In some embodiments, said antimicrobial ionomer composition according to the invention is applied as such or as including additional components, such as cross-linking agents, hydrophobic modifiers, water repellents, various stabilizers and surfactants, for coating of host surfaces such as fiber, fabric and bulk material surfaces, including various synthetic semisynthetic and natural fibers, woven fabrics, nonwoven fabrics, knitted fabrics, papers, various polymer surfaces, steel surfaces, various coating surfaces, wood surfaces and fiber, fabric and bulk material surfaces the like with the composition according to the invention.

In some embodiments, the ionomer compositions according to the invention adhere to a large variety of surfaces very effectively because of the cationic character of the PEI-backbone of the ionomer composition can be used for coating purposes of various substrates. Good adhesion is achieved to, for example, cellulosic products (e.g. cellulose, rayon and viscose), proteins, polyesters, polyamides, chlorine cont. polymers, silicates, silicium dioxide, iron, pigments, paper, wood, cotton, plants, skin, hair, films and fibers. Smooth polyolefin surfaces (PE, PP etc.) may be pretreated to bind certain substrates like coatings, adhesives or polymer films. An effective pretreatment is an oxidative treatment, which produces an exceptionally strong adhesion.

Coating can be achieved through e.g. roll coating, spray coating or bath coating or processes the like. The ionomer composition can be diluted in e.g. alcohols or water or combinations thereof or in other suitable solvent compositions to obtain optimal solutions of the ionomer composition according to the invention in relation to the process in question and required thickness of the ionomer composition according to the invention. Substances assisting the attachment of said ionomer composition according to the invention to surfaces, e.g. cross-linking agents, primer agents or substances the like can be incorporated to the composition. Said assisting substances may be used e.g. as included in the solvent system. In some embodiment said host surfaces may be treated chemically to assist the attachment of the ionomer composition according to the invention, e.g. through oxidation, attachment of substrate/primer layers and methods the like. In some embodiments the ionomer composition of the invention may be covalently cross-linked to and on host surfaces.

Generally, after dilution, the silver concentration of the diluted composition is from $\frac{1}{5}$ to $\frac{1}{1000}$ parts by weight of that of the original composition.

In some other embodiments, the antimicrobial ionomer composition according to the invention is used as an antimicrobial additive in various liquid product matrixes (host materials) compatible with said antimicrobial ionomer composition. The antimicrobial ionomer composition according to the invention can be added into said host materials e.g. during a suitable unit process in association with their production processes, or as a finishing step, naturally depending on the material and process. According to the invention, new antimicrobial materials may be formed through the interaction of the antimicrobial ionomer composition according to the invention (when used as an antimicrobial additive) and said host material. In some embodiments said ionomer composition according to the invention is used as an additive for liquid product matrixes or intermediate product matrixes to form new antimicrobial materials and products.

The "liquid product matrixes" in this context mean any liquid product or intermediate product regardless of its use, its interaction with said antimicrobial additive composition and the final state of matter after usage. In some embodiments the ionomer composition of the invention may be cross-linked with the components of the host matrix. Some exemplifying applications wherein said ionomer composition according to the invention can be used as an antimicrobial additive and/or component for formation of new antimicrobial materials include the following: detergents (e.g. cosmetic/hygienic detergents, shower gels, shampoos and industrial detergents), paints, varnishes, floor conditioners/polishes, adhesives, gelcoats, epoxy materials, polyurethanes, cosmetic products, disinfection substances (e.g. disinfection hand gels, hospital, public space and consumer applications, medical devices, liquids for moist wipes), seaming materials, medicinal products, toothpastes and applications the like.

The examples presented in the following are not meant to limit the scope of the invention.

Example 1

An antimicrobial composition according to the invention was produced in a solvent matrix. 2.0 grams of a branched polyethyleneimine (Lupasol WF, BASF, MW 25 000) was solubilized in 8 grams of ethyl alcohol and cooled down. The solution was reacted together with 0.295 grams of silver chloride by mixing said suspension at room temperature until a clear solution was formed. The obtained ionomer composition had a dry content (mass of the solvent excluded) of 22.3% (w/w) and theoretical silver content of 9.7% (w/w) of dry mass.

Example 2

An antimicrobial ionomer composition according to the invention was produced in a solvent matrix. Approximately 2.0 g of a branched polyethyleneimine (Lupasol G20 waterfree, BASF, molecular weight 1300) was mixed with 6 g of ethyl alcohol and cooled down. The solution was reacted with 0.724 g of silver saccharinate by mixing said suspension at room temperature until a clear solution was formed. The process was continued by adding 2.49 ml of 1 M hydrochloric acid into said solution under continuous mixing. A clear solution of an optically clear ionomer composition was formed, having a dry content (w/w) of 25.0% and theoretical silver content of 9.5% (w/w) of dry mass.

Example 3

An antimicrobial ionomer composition according to the invention was produced in a solvent matrix. 1.0 grams of a branched polyethyleneimine (Lupasol G20 waterfree, BASF, molecular weight 1300) was solubilized to 3 grams of ethyl alcohol and cooled down. The solution was reacted together with 0.156 grams of silver saccharinate by mixing said suspension at room temperature until a clear solution was formed. The process was continued by diluting the intermediate composition to a total volume of 50 ml with EtOH. Finally, the product was chloridized by adding 0.570 ml of 1 M HCl under mixing conditions.

Comparison Example 4

An antimicrobial composition was produced in a solvent matrix. 1.0 grams of a branched polyethyleneimine (Lupasol G20 waterfree, BASF, molecular weight 1300) was solubilized to 3 grams of ethyl alcohol and cooled down. The solution was reacted together with 0.156 grams of silver saccharinate by mixing said suspension at room temperature until a clear solution was formed. The product was diluted to a total volume of 50.570 ml with EtOH.

Example 5

An antimicrobial ionomer composition according to the invention was produced in a solvent matrix. 3.0 grams of a branched polyethyleneimine (Lupasol PS, BASF, molecular weight 750,000, concentration in water 33%) was mixed with 1 grams of ethyl alcohol and cooled down. The solution was reacted together with 0.156 grams of silver saccharinate by mixing said suspension at room temperature until a clear solution was formed. The intermediate composition was diluted to a total volume of 50 ml with EtOH. Finally, the composition was chloridized by adding 0.570 ml of 1 M HCl under mixing conditions.

Comparison Example 6

An antimicrobial composition was produced in a solvent matrix. 3.0 grams of a branched polyethyleneimine (Lupasol PS, BASF, molecular weight 750,000, concentration in water 33%) was mixed with 1 grams of ethyl alcohol and cooled down. The solution was reacted together with 0.156 grams of silver saccharinate by mixing said suspension at room temperature until a clear solution was formed. The product was diluted to a total volume of 50.570 ml with ethyl alcohol.

Application Example 7

The antimicrobial ionomer composition according to the invention produced as described in Example 2 was applied as an antimicrobial additive for an acrylic interior paint (Tikkurila Harmony, white, determined dry mass 88% w/w). Two test batches were prepared by mixing the composition according to Example 2 and the paint in mixing ratios of 1:10 and 1:20, respectively. The resulting theoretical silver contents (% of dry weight) were correspondingly about 0.3% and 0.14%.

For both samples, test surfaces were prepared by painting two surfaces of a PVC film with the sample compositions and the allowed to dry at standard temperature for 48 hours. The antimicrobial efficacy of the paint surfaces against Methicillin Resistant *Staphylococclus Aureus* (MRSA) were determined following standard ISO 22196. As a result for the two paint surfaces, a reduction of >4 log for MRSA was achieved.

Application Example 8

The antimicrobial ionomer composition according to the invention produced as described in Example 2 was applied as an antimicrobial additive for a waxed floor conditioning and polishing agent (Johnson Diversey, Jontec, determined dry mass 28.6% w/w). A test batch was prepared by mixing the ionomer composition according to Example 2 and the floor conditioning and polishing agent in a mixing ratio of 1:10 resulting in theoretical silver content (% of dry weight) of 0.84%. A test surface was prepared. A working solution was prepared by further diluting the test batch with tap water in a ratio of 1:20 (composition according to example 2: Jontec). The dilution was spread on a PVC film and let dry for 48 hours leaving a faint colorless dry material film on the surface. The antimicrobial efficacy of the conditioned surface against Methicillin Resistant *Staphylococclus aureus* (MRSA) was determined following standard ISO 22196. As a result for the surface treated with the diluted floor conditioner doped with the antimicrobial composition according to the invention, a reduction of >4 log for MRSA was achieved.

Application Example 9

The antimicrobial ionomer composition according to the invention produced in examples 3 and 5 and the compositions produced in comparative examples 4 and 6 were applied as an antimicrobial coating/antimicrobial finish for knitted fabric. Four sample pieces (2.5×15 cm$^2$) of a polyester-cotton blend (65%-35%) medical scrub fabrics were treated with the compositions obtained in examples 3 (AE91, 4 (AE92), 5 (AE93) and 6 (AE94). The sample fabrics were immersed into the diluted solutions for 30 seconds. The immersed samples were let dry overnight at room temperature on paper tissues. The antimicrobial efficacy against *Staphylococcus aureus* (ATCC 6538) was tested following ISO 20645-standard. The results are presented in Table 1.

TABLE 1

| Sample | Vinson's rating | Antimicrobial efficacy |
| --- | --- | --- |
| AE91 | 4+ (2 mm) | Excellent |
| AE92 | 2 | Fair |
| AE93 | 4+ (2 mm) | Excellent |
| AE94 | 2 | Fair |

According to the results presented in Table 1, the antimicrobial efficacies of chloridized ionomer compositions, turned out to be higher compared to the compositions obtained through reacting solely PEI and silver saccharinate.

Application Example 10

A series of antimicrobial treatments was carried out for nonwoven polypropylene (19.9 g/m$^2$) fabric (4 samples, AE101-AE104) and polyester-cotton (65%-35%) blend (212.5 g/m$^2$) medical scrub fabric (4 samples, AE105-AE108). An antimicrobial ionomer composition according to the invention was produced in a solvent matrix. 2.0 grams of a branched polyethyleneimine (Lupasol G20 waterfree, BASF, molecular weight 1300) was solubilized to 6.0 grams of ethyl alcohol and cooled down. The solution was reacted together with 0.3 grams of silver saccharinate by mixing said suspension at room temperature until a clear solution was formed. The process was continued by adding 1.140 ml of 1 M hydrochloric acid into said solution. A clear solution of an optically clear ionomer composition was formed, having a dry content (w/w) of 24.8% and theoretical silver content of 4.7% (w/w) of dry mass. A series of baths containing antimicrobial ionomer compostition of the invention obtained previously were prepared. The bath compositions are presented in Table 2.

TABLE 2

| Bath | Dilution (AM-comp.:EtOH) | AM-Comp. (g/l) | Ag (mg/l) |
| --- | --- | --- | --- |
| 1 | 1:20 | 11.50 | 541 |
| 2 | 1:50 | 4.60 | 216 |
| 3 | 1:100 | 2.30 | 108 |
| 4 | 1:200 | 1.15 | 54 |

The fabric samples were treated with the antimicrobial ionomer composition by immersing the sample fabrics into the diluted solutions. Immersed samples were let dry on paper tissues absorbing part of the excess liquid. Resulted mass percentages of antimicrobial coatings and theoretical silver contents of the treated fabrics are listed in Table 3.

TABLE 3

| Sample/Bath | Material | AM-Comp (% w/w) | Ag (mg/m$^2$) |
| --- | --- | --- | --- |
| AE101/1 | nonwoven PP | 6.20 | 54 |
| AE102/2 | nonwoven PP | 3.26 | 26 |
| AE103/3 | nonwoven PP | 0.83 | 8 |
| AE104/4 | nonwoven PP | 0.40 | 4 |
| AE105/1 | cotton-PE blend | 1.55 | 155 |
| AE106/2 | cotton-PE blend | 0.84 | 84 |
| AE107/3 | cotton-PE blend | 0.39 | 39 |
| AE108/4 | cotton-PE blend | 0.33 | 33 |

The antimicrobial efficacies of treated sample fabrics coated with the antimicrobial composition of the invention were tested against Staphylococous aureus (ATCC 6538) following ISO 20743-standard. The results are presented in Table 4.

TABLE 4

| Sample | Vinson's rating | Antimicrobial efficacy |
|---|---|---|
| AE101 | 4 | Excellent |
| AE102 | 2 | Fair |
| AE103 | 2 | Fair |
| AE104 | 2 | Fair |
| AE105 | 4 (+2) | Excellent |
| AE106 | 4 (+1) | Excellent |
| AE107 | 4 | Excellent |
| AE108 | 4 | Excellent |

It must be noted that the applied microbiological test has limitations when tested with a very lightweight fabrics, such as CE 101-104. By taking into account the limitations, very successful antimicrobial performances were achieved for all samples.

Example 11

An antimicrobial ionomer composition according to the invention was produced in a solvent matrix. 2.0 grams of a branched polyethyleneimine (Lupasol WF, BASF, MW 25,000) was solubilized in 8 grams of ethyl alcohol and cooled down. The solution was reacted together with 0.295 grams of silver chloride by mixing said suspension at room temperature until a clear solution was formed. The process was continued by adding 0.378 grams of saccharin and mixing until a clear solution was formed.

Example 12

An antimicrobial ionomer composition according to the invention was produced in a solvent matrix. 2.0 grams of a branched polyethyleneimine (Lupasol P, BASF, MW 750,000, concentration in water 50%) was mixed with 5.460 grams of ethyl alcohol and cooled down. The solution was reacted together with 0.345 grams of silver chloride by mixing said suspension at room temperature until a clear solution was formed. The process was continued by adding 0.5 grams of saccharin.

Example 13

An antimicrobial ionomer composition according to the invention was produced in a solvent matrix. 160 grams of a branched polyethyleneimine (Lupasol WF, BASF, MW 25,000) was solubilized to 640 grams of ethyl alcohol and cooled down. The solution was reacted together with 23.64 grams of silver chloride by initially homogenizing said product with a high shear homogenizer for one minute and further mixing said suspension at room temperature under agitation by a magnetic stirrer until a clear solution was formed. The process was continued by adding 35.21 grams of saccharin followed by mixing until a clear transparent composition was formed.

Example 14

An antimicrobial ionomer composition according to the invention was produced in a solvent matrix. 2.1 grams of a branched polyethyleneimine (Lupasol WF, BASF, MW 25,000) was solubilized in 1000 ml of deionized water. The solution was reacted together with 0.3 grams of silver chloride, 0.16 grams of saccharin and 2 grams of ammonium chloride at room temperature resulting in a clear ionomer solution.

Example 15

An antimicrobial ionomer composition according to the invention was produced in a solvent matrix. 4 grams of polyvinylamine (Catiofast GM, BASF) and 22.32 grams of a branched polyethyleneimine (Lupasol WF, BASF, MW 25 000) was solubilized in 80.86 grams of isopropanol and cooled down. The solution was reacted together with 3.88 grams of silver chloride by mixing said suspension at room temperature until a clear solution was formed. The process was continued by adding 2.08 grams of saccharin and mixing until a clear solution was formed.

Example 16

An antimicrobial ionomer composition according to the invention was produced in a solvent matrix. 26.26 grams of a branched polyethyleneimine (Lupasol WF, BASF, MW 25 000) was solubilized in 80.86 grams of isopropanol. The solution was reacted together with 3.88 grams of silver chloride by mixing said suspension at a constant temperature of 16° C. until a clear solution was formed. The process was continued by adding 2.08 grams of saccharin and mixing until a clear solution was formed.

Application Example 17

An antimicrobial ionomer composition according to the invention may be applied as an antimicrobial finish/topical treatment/coating agent for various fibers and fiber products, including natural (e.g. cotton), semisynthetic (e.g. viscose) and synthetic (e.g. PET, PS, nylon, polyamide, polyacrylonitrile etc.) fibers and fiber products as applied as such or in combination (as reacted or unreacted), with various fiber/yarn/textile treatment additives, modifiers, spin bath additives, finishes, lubricants, cross-linking agents, dyes, coating agents, flame retardant agents and the like. It is clear, that various material combinations used in combination with the antimicrobial ionomer composition produce varying properties to the finished fibers with respect to water solubility of the final finish composition on the fiber surfaces, silver release and correspondingly antimicrobial function.

In the example, an antimicrobial ionomer composition according to Example 16 was applied as an antimicrobial fiber finish with viscose fiber as an example material. The antimicrobial composition was applied together with an exemplifying series of fiber and textile treatment agents of different types, in more detail, with a finish agent for water- and oil repellent finish of synthetic and celluosic fibers and textiles (Nuva 2110, Clariant), a low foaming lubricant for cellulosic fibers (Imacol C), an optical brightener for cellulosic fibers (Leucophor BFB, Clariant), a viscose process additive/cleaning agent (Afilan ZS, Clariant) and a viscose nonwoven finish (Afilan HSGV, Clariant).

Aqueous fiber finish/treatment baths FB1-FB5 with compositions according to Table 5 were prepared. In association with each bath, a 3.3 g sample of dry viscose fiber (1.3 dtex) was pre-moistured with water and immersed into the bath (T=60° C., volume 100 ml) for 3 minutes. Excess finish solution was removed from the fiber mass of each sample through pressing until a moisture content of 50% (wet weight of the sample approximately 6.6 grams) was obtained. All the samples were dried at 80° C. for 40 minutes and carded.

TABLE 5

| Sample/Bath | Components | Concentration in water |
|---|---|---|
| AE171/FB1 | AM Comp. | 0.5% (v/v) |
| | Nuva 2110 | 0.5% (w/w) |
| AE172/FB2 | AM Comp. | 0.5% (v/v) |
| | Imacol C | 0.5% (w/w) |
| AE173/FB3 | AM Comp. | 0.5% (v/v) |
| | Leucophor BFB | 0.5% (w/w) |
| AE174/FB4 | AM Comp. | 0.5% (v/v) |
| | Afilan ZS | 0.5% (w/w) |
| AE175/FB5 | AM Comp. | 0.5% (v/v) |
| | Afilan HSGV | 0.5% (w/w) |

The finished and carded fiber samples were subjected to a quantitative analysis of antimicrobial efficacy according to the international standard ISO 20743:2007 (Textiles-Determination of antibacterial activity of antibacterial finished products). The results are presented in Table 6.

TABLE 6

| Sample/Bath | Antibacterial activity value (ISO 20743:2007) |
|---|---|
| AE171/FB1 | >4.5 |
| AE172/FB2 | 3.2 |
| AE173/FB3 | >4.5 |
| AE174/FB4 | 3.1 |
| AE175/FB5 | >4.3 |

Various fiber and fabric finish bath compositions comprising the antimicrobial composition and heat applied in combination with the drying process may naturally affect the properties of the specific chemical structure of the finish combination (AM ionomer composition and other components of a specific bath) through e.g. inducing covalent bonding between functional groups of the finish agents and those incorporated to the fiber or fabric. This again may alter the electrical charge and water solubility of the final fiber surface finish composition and correspondingly increase the wash durability of the finished fiber and the textile products produced thereof.

Application Example 18

An antimicrobial ionomer composition according to Example 16 was applied as an aqueous dilution as an antimicrobial fiber finish agent together with water- and oil-repellent finish of synthetic and celluosic fibers and textiles (Nuva 2110, Clariant). The thermal and UV tolerance of the AM ionomer composition was further increased with ammonium chloride and sodium saccharin dihydrate as included in the composition as stabilizers. A 100 ml finish bath according to Table 7 was prepared.

TABLE 7

| Sample/Bath | Components | Concentration in water |
|---|---|---|
| AE181/FB6 | AM comp. | 0.5% (v/v) |
| | Nuva 2110 | 0.5% (w/w) |
| | NH$_4$Cl | 0.3% (w/v) |
| | Sodium saccharin dihydrate | 0.2% (w/v) |

A viscose fiber (1.3 dtex) sample AE181 of 3.3 grams was treated with bath FB6 following similar steps and conditions as described in Example 17, however as dried at a temperature of 120° C. for 10 minutes. The antibacterial activity of the antibacterial finished fiber sample AE181 was measured according to international standard ISO 20743:2007. As a result, an excellent antibacterial activity value of 3.9 was achieved for the sample.

Application Example 19

An antimicrobial ionomer composition according to Example 16 was applied as an antimicrobial fiber finish agent together with two water dispersible crosslinking agents. Various crosslinking agents used together with amine functional polymers result in covalently bonded fiber finish structures decreasing the water solubility of the dried finish matrix. In the example, epichlorohydrin and dipropylene glycol based epoxy resin (D.E.R 736P, Dow) and a water dispersible polyisocyanate (Easaqua X D 803, Perstorp) were applied as crosslinking agents. A fiber treatment bath solution FS3 according to Table 8 was prepared.

TABLE 8

| Sample/Solution | Components | Concentration in water |
|---|---|---|
| AE191/FB7 | AM comp. | 0.5% (v/v) |
| | Perstorp Easaqua X D 803 | 0.18% (v/v) |
| | Dow D.E.R 803 | 0.23% (v/v) |

A viscose fiber (1.3 dtex) sample AE191 of 3.3 grams was treated with bath FB7 following similar steps and conditions as described in Example 17.

The antibacterial activity of the antibacterial finished fiber was measured according to international standard ISO 20743:2007. As a result, an excellent antibacterial activity value of 3.9 was achieved for the sample.

Application Example 20

An antimicrobial ionomer composition according to Example 16 was applied as an antimicrobial fiber finish agent as combined with a self-emusifiable polyisocyanate-type crosslinking agent in a sequential multibath setup. Three 100 ml aqueous fiber treatment baths FB8.1-FB8.3 with compositions according to Table 8 were prepared. In the bath FS4.1 heat and UV tolerance of the antimicrobial ionomer composition was increased by incorporating ammonium chloride to the composition. The Bath FB4.2 comprised the aqueous solution of a di-isocyanate type crosslinking agent.

TABLE 9

| Sample/Bath | Components | Concentration in water |
|---|---|---|
| AE201/FB8.1 | AM comp. | 0.5% (v/v) |
| | NH$_4$Cl | 0.2% (w/v) |
| AE201/FB8.2 | Perstorp Easaqua X D 803 | 0.2% (v/v) |
| AE201/FB8.3 | Only H$_2$O | |

A 3.3 g sample of dry viscose fiber (1.3 dtex) was pre-moistured with water and immersed sequentially into baths FB8.1-FB8.3 (for all baths: T=60° C., volume 100 ml) for 3 minutes per bath. Excess finish solution was removed from the fiber mass after each bath throgh pressing until a moisture content of 50% (wet weight of the sample approximately 6.6 grams) was obtained. Finally, the sample was dried at 100° C. for 30 minutes and carded. The antibacterial activity of the antibacterial finished carded fiber was measured according to international standard ISO 20743:2007. As a result, an excellent antibacterial activity value of >4.3 was achieved with the sample.

Application Example 21

The antimicrobial ionomer composition in accordance with the invention can be applied as an antimicrobial and deodorizing agent and additive in multiple surface disinfection and sanitizing compositions and products including e.g. surface desinfection, hand disinfection, shoe and clothing deodorant and wet wipe liquid products and compositions and the like.

One of the unique advantages provided by the antimicrobial ionomer composition in surface treatment applications is the thin ionomeric layer provided on the treated surfaces, leaving the surfaces microbicidal after evaporation of the liquid solvents.

As an example, isopropyl alcohol was applied as a simplified example surface disinfection product and the antimicrobial ionomer composition was applied as an antimicrobial surface treatment additive component forming a dilute antimicrobial ionomer composition according to the invention. A stock solution of antimicrobial ionomer composition was prepared similarly to Example 16, however by using a cosmetic grade SP-012 (Nippon Shokubai) polyethyleneimine. The stock composition was further diluted into an example product concentration with 200 parts of isopropyl alcohol. The bactericidal activity of the example surface disinfection product was tested following the standard EN 13697:2001 (a quantitative non-porous surface test for the evaluation of bactericidal and/or fungicidal activity of chemical disinfectants) showing >log 5.8 (0 cfu after treatment=practically sterile) reduction for *Staphylococcus aureus*. The antimicrobial function of the thin antimicrobial ionomer layer left on the treated surface was demonstrated as follows: a film of the composition was spread onto the surface of a sterile 5×5 cm PVC sheets through dip coating. Three similarly prepared replicate samples were dried for 24 hours at room temperature. The antimicrobial efficacy of the treated surface was tested following the international standard ISO 22196. The results indicated a log 4 reduction for *Staphylococcus aureus*.

The invention claimed is:

1. An antimicrobial ionomer solution comprising an ionomer, the ionomer comprising an amine functional cationic polymer compound and silver chloride, wherein said amine functional polymer comprises branched polyethyleneimine having a molecular weight (Mw) between 200 and 3,000,000.

2. The antimicrobial ionomer solution according to claim 1, further comprising a stabilizer substance, wherein the stabilizer substance comprises saccharin or a salt of saccharin.

3. The antimicrobial ionomer solution according to claim 1, wherein silver chloride is in molecular form.

4. The antimicrobial ionomer solution according to claim 1, further comprising a solvent matrix formed by an alcohol, water, or a combination thereof.

5. The antimicrobial ionomer solution according to claim 4, wherein said solvent matrix comprises a member from the group consisting of methyl alcohol, ethyl alcohol, propyl alcohol, butyl alcohol, water, and combinations thereof.

6. The antimicrobial ionomer solution according to claim 1, obtainable by reacting together:
70 to 99.99 parts by weight of the branched polyethyleneimine and
0.01 to 30 parts by weight of the silver chloride.

7. The antimicrobial ionomer solution according to claim 6, wherein said polyethyleneimine and silver chloride are further reacted together with at least one stabilizer substance.

8. The antimicrobial ionomer solution according to claim 7, wherein the at least one stabilizer substance comprises saccharin or a saccharin salt.

9. The antimicrobial ionomer solution according to claim 6, wherein said reacting is carried out in a solvent matrix.

10. The antimicrobial ionomer solution according to claim 1, wherein said solution is internally cross-linked through at least one cross-linking agent.

11. The antimicrobial ionomer solution according to claim 1, wherein the composition has a silver content of about 0.01 to 50% by weight of the total weight of the composition.

12. The antimicrobial ionomer solution according to claim 1, wherein the solution has a weight ratio of the silver chloride to the branched polyethyleneimine of about 1:100 to 100:1.

13. The antimicrobial ionomer solution according to claim 1, further comprising a stabilizer substance, wherein the stabilizer substance is a compound comprising ammonium cations, saccharin, or an organic substance carrying sulfonamide functional group(s).

14. The antimicrobial ionomer solution according to claim 1, further comprising a stabilizer substance, wherein the stabilizer substance is selected from the group consisting of saccharin, cyclamic acid, sulfadiazine, acesulfame and their alkali metal or ammonium salts or complex derivatives, ammonium chloride and alkali metal chlorides.

15. The antimicrobial ionomer composition according to claim 1, wherein the ionomer composition comprises an optically clear solution.

\* \* \* \* \*